(12) United States Patent
Lev et al.

(10) Patent No.: US 6,895,625 B2
(45) Date of Patent: May 24, 2005

(54) AUTOMATIC ELECTRIC TOOTHBRUSH

(75) Inventors: Mordechai Lev, Northville, MI (US); Roman S. Ferber, West Bloomfield, MI (US)

(73) Assignee: HoMedics, Inc., Commerce Township, MI (US)

(*) Notice: Subject to any disclaimer, the term of this patent is extended or adjusted under 35 U.S.C. 154(b) by 214 days.

(21) Appl. No.: 10/106,403

(22) Filed: Mar. 26, 2002

(65) Prior Publication Data

US 2003/0000033 A1 Jan. 2, 2003

(51) Int. Cl.⁷ .............................................. A61C 17/22
(52) U.S. Cl. ...................... 15/28; 15/22.1; 200/42.01; 200/61.42; 200/61.58 R
(58) Field of Search ............................... 15/22.1–22.4, 15/23, 28; 200/42.01, 52 R, 61.41, 61.42, 61.58 R, 61.85, 332.3, 511, 512, 600

(56) References Cited

U.S. PATENT DOCUMENTS

| | | | |
|---|---|---|---|
| 3,551,932 A | * 1/1971 | Grossman ..................... 15/23 |
| 3,822,432 A | * 7/1974 | Skinner ........................ 15/23 |
| 3,848,336 A | 11/1974 | Copeland ..................... 433/99 |
| 3,859,684 A | 1/1975 | Moskwinski ................. 15/23 |
| 3,939,599 A | 2/1976 | Henry et al. ................. 433/99 |
| 4,192,035 A | 3/1980 | Kuris .......................... 15/22.1 |
| 4,458,702 A | 7/1984 | Grollimund ................. 132/322 |
| 4,882,801 A | 11/1989 | Benz ........................... 15/23 |
| 5,282,291 A | 2/1994 | Spieler et al. ............. 15/167.1 |
| 5,453,644 A | 9/1995 | Yap et al. ................... 307/116 |
| 5,502,861 A | 4/1996 | Spieler et al. ............. 15/167.1 |
| 5,577,285 A | 11/1996 | Drossler ..................... 15/22.1 |
| 5,625,916 A | 5/1997 | McDougall .................. 15/28 |
| 5,680,666 A | 10/1997 | Ra ............................. 15/97.2 |
| 5,836,030 A | 11/1998 | Hazeu et al. .............. 15/22.1 |
| 5,901,397 A | 5/1999 | Hafele et al. .............. 15/22.1 |
| 6,067,688 A | 5/2000 | West ........................... 15/311 |
| 6,178,579 B1 | 1/2001 | Blaustein et al. ............ 15/28 |
| 6,189,693 B1 | 2/2001 | Blaustein et al. ....... 206/362.2 |
| 6,195,828 B1 | 3/2001 | Fritsch ...................... 15/22.1 |
| 6,237,178 B1 | 5/2001 | Krammer et al. .......... 15/22.1 |
| 6,308,358 B2 | 10/2001 | Gruber et al. ............. 15/22.1 |
| 6,308,359 B2 | 10/2001 | Fritsch et al. ............. 15/22.1 |
| 6,327,734 B1 | 12/2001 | Meginniss, III et al. ..... 15/105 |

* cited by examiner

*Primary Examiner*—Mark Spisich
(74) *Attorney, Agent, or Firm*—Brooks Kushman P.C.

(57) ABSTRACT

An motorized electric toothbrush includes a removable brush head and a switch that allows the toothbrush to be used in an "automatic" mode. The "automatic" mode provides for intermittent motorized operation, such that when the brush head contacts the operator's teeth, a switch is actuated and the motor is engaged. The brush head is easily removed for replacement when the bristles become worn or to allow use of the toothbrush by multiple users.

9 Claims, 8 Drawing Sheets

Fig. 12 TO PC BOARD

Fig. 13

AUTOMATIC ELECTRIC TOOTHBRUSH

BACKGROUND OF THE INVENTION

1. Field of the Invention

The present invention relates to a motorized electric toothbrush with a multi-position switch allowing for an automatic mode of operation.

2. Background Art

Use of motorized electric toothbrushes used as an aid in cleansing teeth is well known. Typically these toothbrushes employ rotating, reciprocating, or oscillating motion, or a combination thereof, to effectuate the cleaning process.

A feature commonly found on these toothbrushes is an on/off switch located on or near the handle portion of the toothbrush. The primary feature of such a switch is that it remains either in the "on" position or the "off" position until the user manually changes it. With such a switch, the user has a limited number of choices. The toothbrush motor can be engaged prior to the brush head being placed in the mouth, or the user can wait until the brush head is placed within the mouth before engaging the motor. Both of these choices have inherent undesirable consequences.

When the user engages the motor prior to placing the brush head in the mouth, the rapid movement of brush head may cause the toothpaste to be shaken off the bristles. Conversely, if the user waits until the brush head is inside the mouth, and in particular in contact with the teeth, it may be difficult to engage the switch, depending on its position relative to the user's hand.

Another feature commonly found in motorized electric toothbrushes is a removable brush head section. This allows the brush head section to be replaced when the bristles become worn, and also allows the same toothbrush to be shared by multiple users. Typically, a removable brush head section attaches to the toothbrush handle and contains linkages to transfer mechanical power from the motor to a bristle section. Different types of attachments and linkages are known in the art, with particular mechanisms chosen to achieve particular results. For example, U.S. Pat. No. 6,308,359 issued to Fritsch et al. on Oct. 30, 2001 describes a motorized electric toothbrush having a removable brush section with an attachment mechanism intended to reduce noise and vibrations. Another example is found in U.S. Pat. No. 5,836,030 issued to Hazeu et al. on Nov. 17, 1998. Hazeu et al. describes a motorized electric toothbrush having a removable brush attachment with linkages designed to induce specific bristle motions.

The patents referenced above are just two examples of the various types of removable brush head toothbrushes. Despite their varied and widespread use, each of the known designs contains the same limitation: once the motor is turned on, it operates continuously until it is turned off. None of these designs include an automatic mode of operation that provides for motorized operation only when the toothbrush is being used by an operator.

Accordingly, it is desirable to provide an improved motorized electric toothbrush that overcomes the above referenced shortcomings of prior art toothbrushes, by including on the toothbrush a removable head portion and further providing for an automatic mode of operation that allows the motor to operate only when the toothbrush is being used by an operator.

SUMMARY OF THE INVENTION

One aspect of the present invention provides a motorized electric toothbrush that is operable in an automatic mode, such that the motor only engages when the brush head is in contact with the operator's teeth.

Another aspect of the invention provides a motorized electric toothbrush that is operable in an automatic mode and has a removable head portion to facilitate replacement when the bristles are worn, and to allow use of the toothbrush by multiple users.

Accordingly, a motorized electric toothbrush is provided that comprises a handle portion that has a first housing, and a removable head portion that has a bristle head and a second housing and is selectively attachable to the handle portion. A switch has a first position for preventing motorized operation of the toothbrush and a second position for facilitating motorized operation of the toothbrush. Exerting pressure on the bristle head places the switch in the second position.

Another aspect of the invention provides a motorized electric toothbrush that comprises a handle portion that has a first housing, and a removable head portion that has a bristle head and a second housing and is selectively attachable to the handle portion. A first switch is disposed within the handle portion having a first position for preventing motorized operation of the toothbrush and a second position for facilitating automatic operation of the toothbrush. A second switch is disposed within one of the housings and actuates when the toothbrush is used by an operator. This causes motorized operation of the toothbrush when the first switch is in the second position.

A further aspect of the invention provides a handle portion that has a first housing, and a removable head portion that has a bristle head and a second housing and is selectively attachable to the handle portion. A first switch is disposed within the handle portion and has a first position for preventing motorized operation of the toothbrush. The first switch also has a second position for facilitating automatic operation of the toothbrush, and a third position for continuous motorized operation of the toothbrush. A second switch is disposed within one of the housings and actuates when the toothbrush is used by an operator. This causes motorized operation of the toothbrush when the first switch is in the second position.

The above object and other objects, features, and advantages of the present invention are readily apparent from the following detailed description of the best modes for carrying out the invention when taken in connection with the accompanying drawings.

BRIEF DESCRIPTION OF THE DRAWINGS

FIG. 3 shows an exploded view of the toothbrush shown in FIG. 1;

DETAILED DESCRIPTION OF THE PREFERRED EMBODIMENT

Figures 1, 2A, 2B:
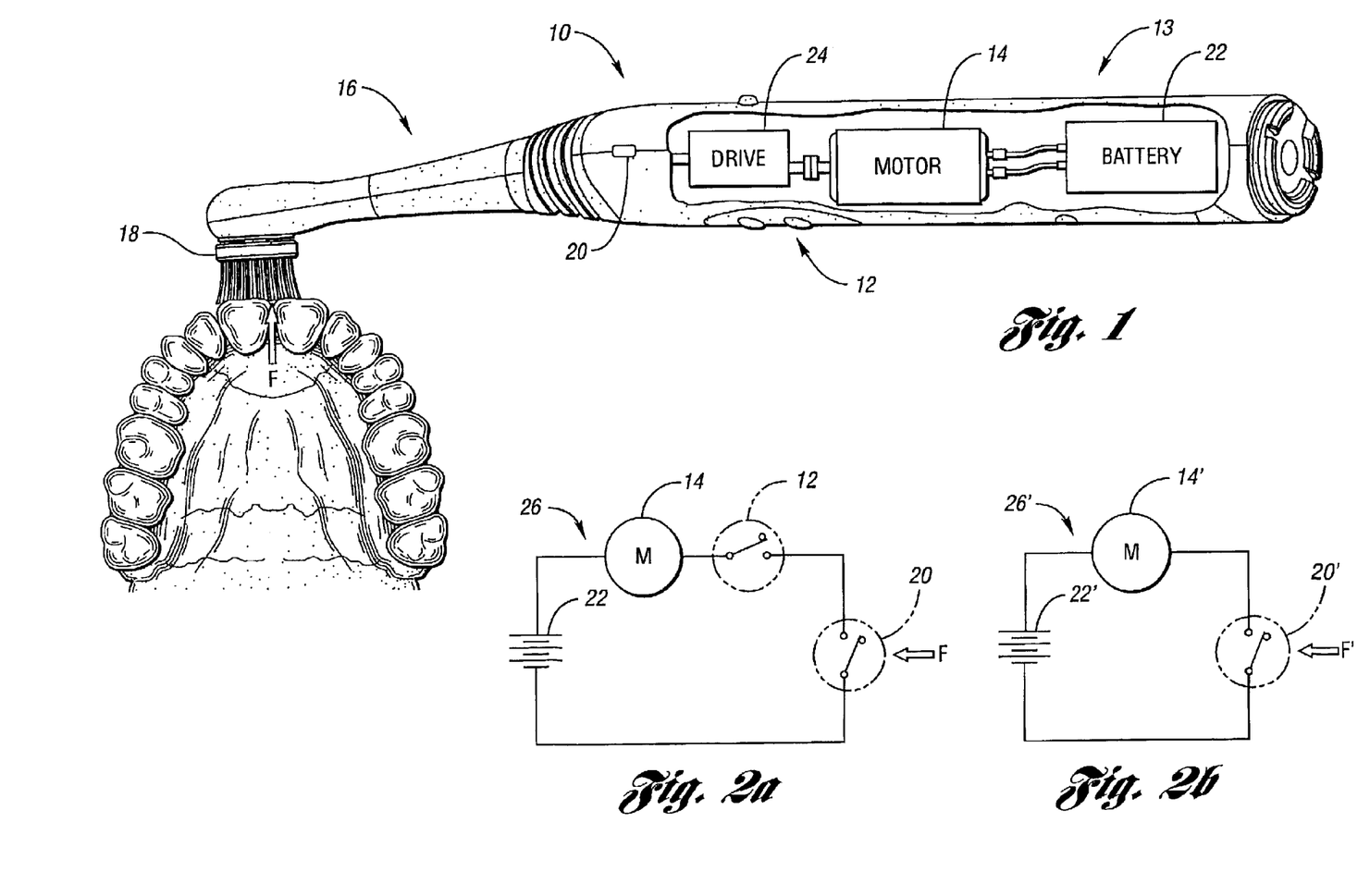
FIG. 1 shows a simplified descriptive side view of an electric toothbrush in accordance with the present invention.
FIG. 2a shows a simple wiring schematic for the toothbrush shown in FIG. 1.
FIG. 2b shows a simple wiring schematic for a toothbrush with only one switch.
Figure 2:
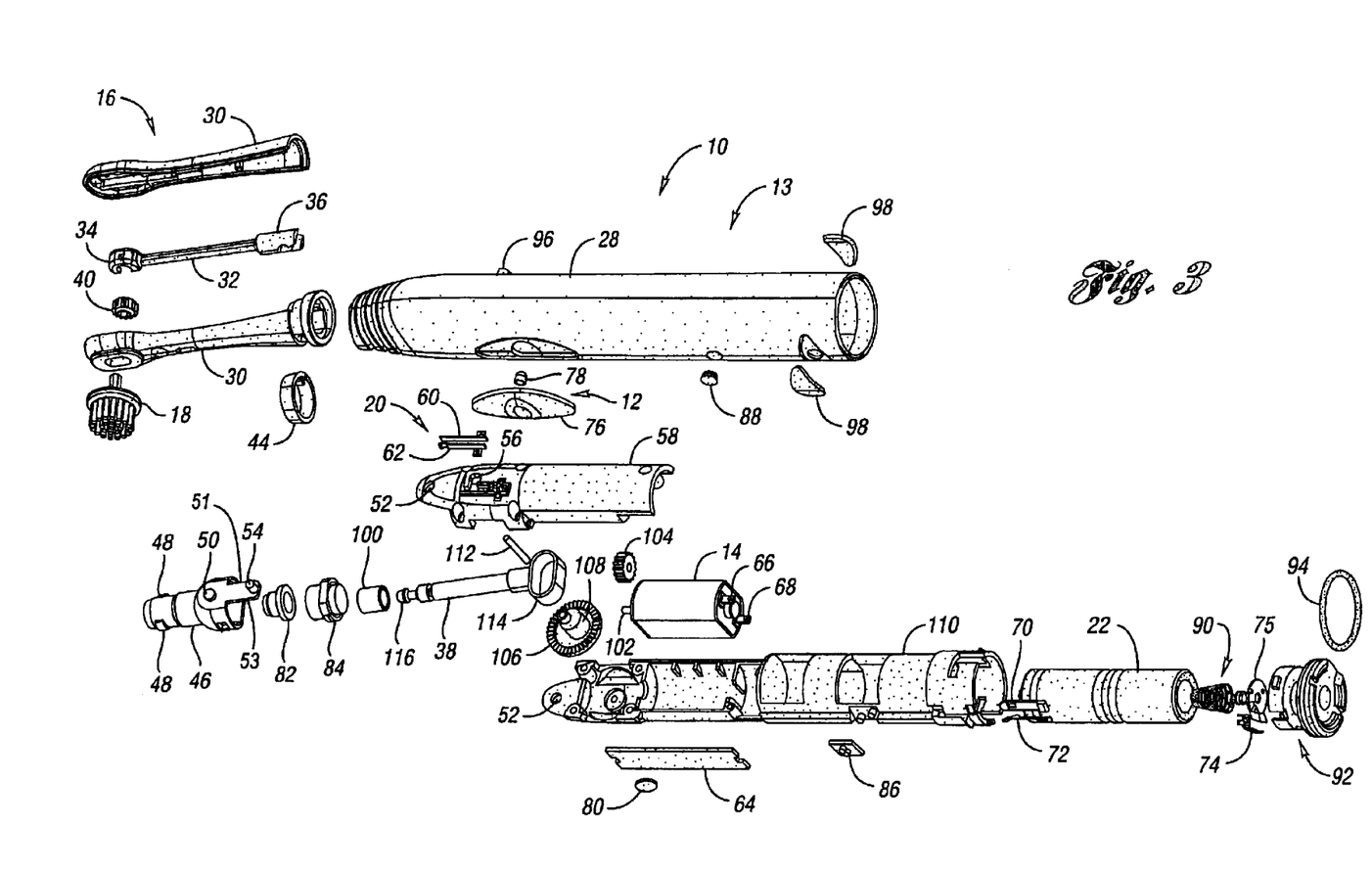

FIG. 1 shows a simplified descriptive side view of an electric toothbrush 10 in accordance with the present invention. A first switch 12, located in a handle portion 13, has two positions: "off" and "automatic". While in the automatic mode, a motor 14 is engaged only when a force (F) is exerted on a removable head portion 16. This occurs when a bristle head 18 sufficiently contacts a user's teeth. As used here and throughout, the term "sufficiently contacts" implies a contact that is sufficient to cause a slight movement of at least a part of the removable head portion 16 in the direction of the force. The force exerted by a user during normal brushing typically constitutes a sufficient contact. Because of the movement of the removable head portion 16, a second switch 20 is actuated, an electric circuit is completed, and current flows from a battery 22 to the motor 14. The motor 14 transmits power to the removable head portion 16 through a series of mechanical linkages, shown in detail in FIG. 3 and partially represented in FIG. 1 as drive 24.

FIG. 2a shows a simple wiring schematic 26 of a circuit for the toothbrush shown in FIG. 1. The motor 14 is electrically connected between the battery 22 and the first switch 12. When the first switch 12 is in the "off" position, the circuit is open and there is no voltage across the motor 14. When the first switch 12 is in the "automatic" position, control of the motor 14 is transferred to the second switch 20. While operating in the automatic mode, the motor 14 is only engaged when a force (F') is applied to the second switch 20, which occurs as a result of the force (F) being applied to the bristle head 18, see FIG. 1. The second switch 20 can be placed in various locations within the toothbrush, such as in the handle portion 13 or under the bristle head 18.

The first switch 12 can be eliminated from the circuit 26, resulting in a circuit 26' shown in FIG. 2b. In this configuration, switch 20' is the only switch in the circuit. When the circuit 26' is used in a toothbrush, the switch 20' can be placed in various locations within the toothbrush, such as in a handle portion or under a bristle head. When the switch 20' is located under the bristle head, the motor 14' is engaged when a force is applied to the bristle head. For example, when there is no force applied to the bristle head, the switch 20' is in a first position and the circuit 26' is open. When the force (F') places the switch 20' in a second position, the circuit 26' is closed and current flows from the battery 22' to the motor 14'. A toothbrush wired with such a circuit is effectively always in the automatic mode. That is, any time a force (F) is applied to the bristle head, the motor 14' is engaged.

The two circuits 26, 26' shown in FIGS. 2a and 2b both allow a toothbrush to be used in an automatic mode. That is, the toothbrush motor is engaged whenever a force is applied to that portion of the toothbrush that contains the second switch 20 or 20'. This facilitates ease of use, eliminating the need to operate a typical slide-button switch after the bristle head is placed in the operator's mouth. Another advantage of a such a configuration is that a consumer can engage the toothbrush motor while the toothbrush is still packaged—i.e., prior to sale. In this way, the consumer can evaluate the operation of the toothbrush before purchase. Some prior art toothbrushes have a multi-function switch configured such that the consumer operates the toothbrush in the package using one activation mode, then operates the toothbrush during normal use in another activation mode. Such is not the case with the present invention, which affords the consumer the opportunity to activate the toothbrush in the package exactly as it will be activated during normal use. In today's consumer savvy environment, this feature provides another advantage over prior art toothbrushes.

Figure 4:
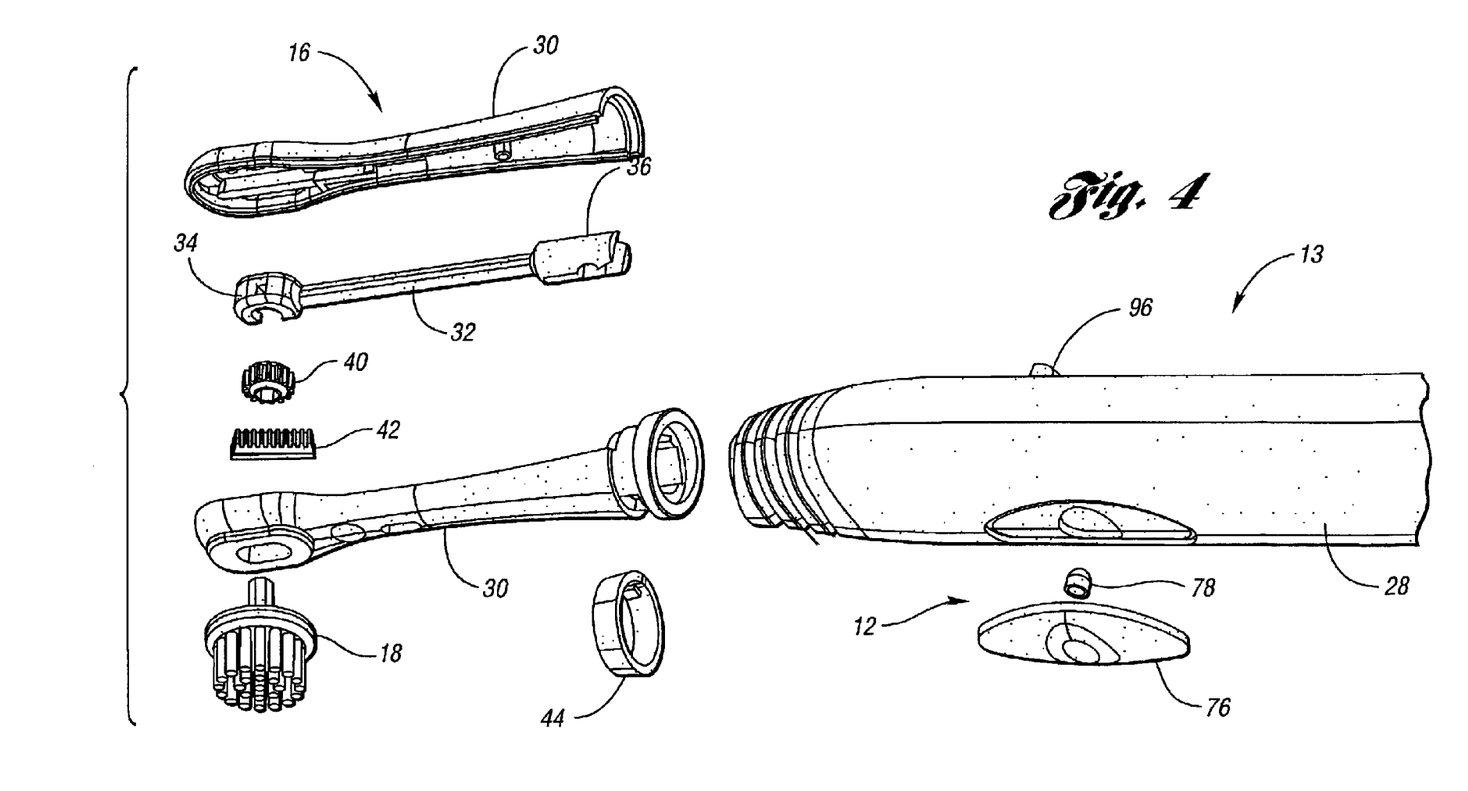
FIG. 4 shows an enlarged exploded view of a portion of the toothbrush shown in FIG. 3, including the removable head portion and part of the handle portion.

FIG. 3 shows an exploded view of the motorized electric toothbrush 10 in accordance with one embodiment of the present invention. The toothbrush 10 includes the handle portion 13 and the removable head portion 16. Many of the components of the handle portion 13 are covered by a first housing 28. Similarly, many of the components of the removable brush head 16 are covered by a second housing 30, which in FIGS. 3 and 4 is shown partially exploded for clarity. The first and second housings 28, 30 will usually be made from a polymeric material, and may be opaque, clear, or translucent. When the first and second housings 28, 30 are clear or translucent, the toothbrush operator may see the movement of some of the toothbrush components when the motor 14 is engaged. In addition, aesthetically pleasing features such as flashing lights (not shown) can be added to the components within the housings 28, 30 to augment the visual appearance. The removable head portion 16 also includes a shaft 32 that on one end has a pinion carrier 34 and on the other a yoke 36 configured to attach to a drive shaft 38. A pinion 40 is attached to the bristle head 18 and interfaces with a rack 42, seen in FIG. 4. Also included in the removable head portion 16 is a snap ring 44 that is manufactured in different colors such that removable brush heads belonging to different users can have different colored snap rings for easy identification.

Figure 5:
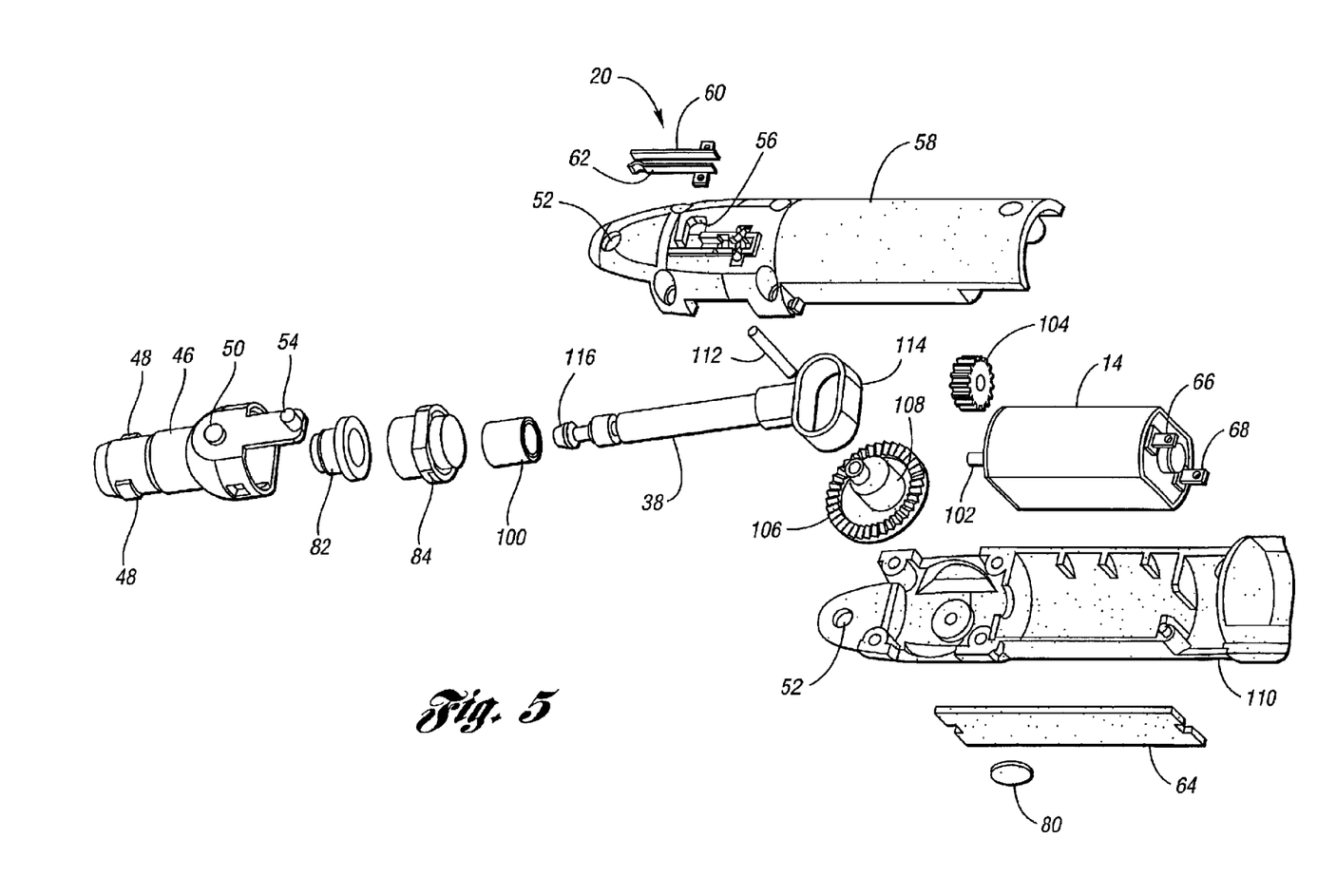
FIG. 5 shows an enlarged exploded view of a portion of the toothbrush shown in FIG. 3, including the motor and drive mechanism.
Figure 6:
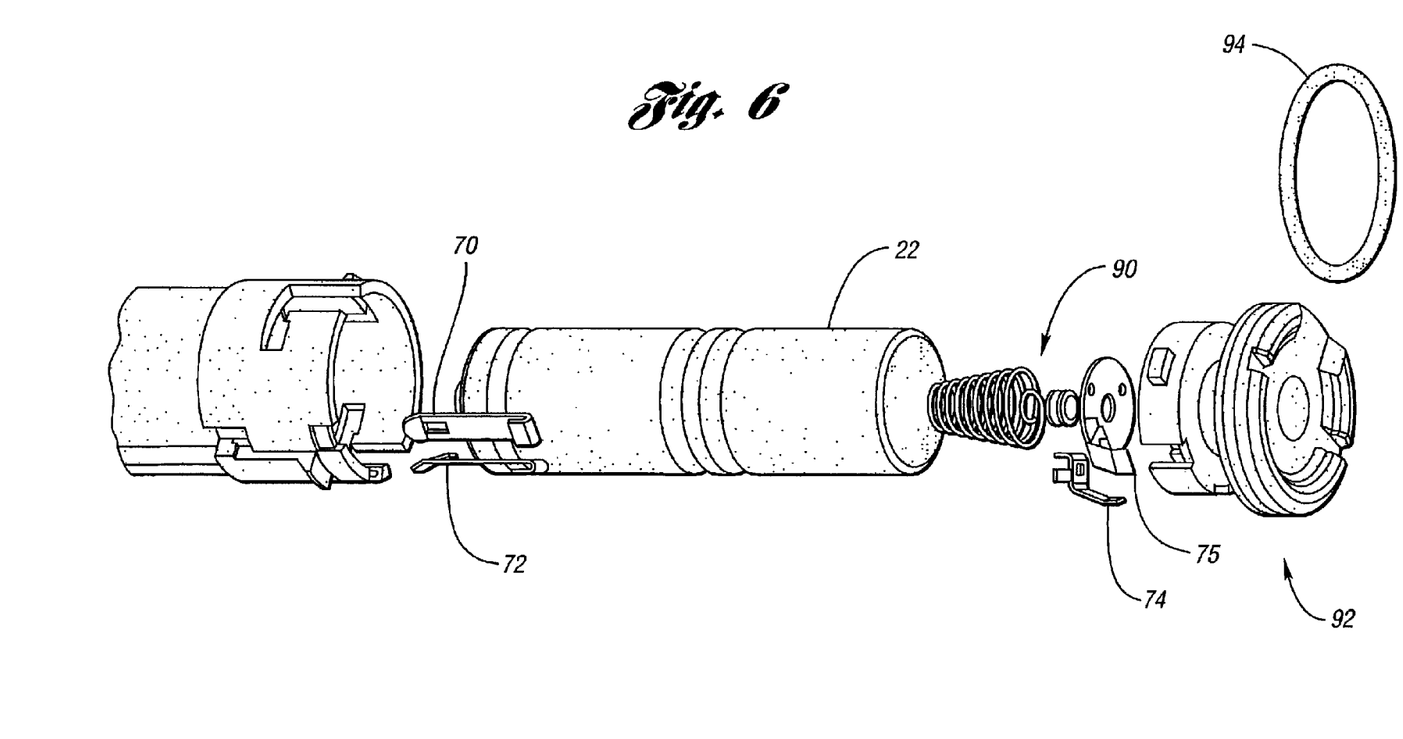
FIG. 6 shows an enlarged exploded view of a portion of the toothbrush shown in FIG. 3, including the battery and end cap.

The components of the handle portion 13 are seen in FIG. 3, with selected components shown enlarged for clarity in FIGS. 4–6. A rocker element 46 serves a number of important functions. First, it contains clips 48 that help secure the removable head portion 16 to the handle portion 13. In addition, trunnions 50, only one of which is visible, rotate in apertures 52 thereby allowing the rocker element 46 to pivot as force is applied to the removable head portion 16. As shown in FIG. 3, the rocker element 46 includes an actuator 51 having an actuator arm 53. As the rocker element 46 pivots about the trunnions 50, a pin 54, located on the actuator arm 53, moves within a slot 56. The slot 56 is located in a first casing portion 58 which also contains one of the apertures 52 in which one of the trunnions 50 rotates. Also located in the first casing portion 58 is the first switch 20, which comprises first and second contact plates 60, 62.

The contact plates 60, 62 are attached to the first casing portion 58 in such a way that movement of the pin 54 within the slot 56 selectively causes the contact plates 60, 62 to contact each other and thereby electrically connect. When the contact plates 60, 62 electrically connect, the second switch 20 is actuated. This means that when the toothbrush 10 is in the automatic mode of operation, electrical connection of the contact plates 60, 62 engages the motor and causes movement of the bristle head 18. Thus, when the toothbrush 10 is in the automatic mode of operation, sufficient contact of the bristle head 18 with the user's teeth will cause a slight deflection of the removable head portion 16. This in turn causes the rocker element 46 to pivot on its trunnions 50 thereby moving the pin 54 within the slot 56. When the pin 54 causes electrical connection of the contact plates 60, 62, the motor 14 is engaged without the user having to manually actuate any additional switches. Hence, motorized operation of the toothbrush 10 is "automatic". The contact plate 60 also acts like a spring, so that when the bristle head 18 is not in contact with the user's teeth, the contact plate 60 pushes against the pin 54 and biases away from the contact plate 62. Thus, the motor 14 disengages when the bristle head 18 is no longer in contact with the user's teeth.

The contact plates 60, 62 are wired to a printed circuit (PC) board 64. Though the wires are removed from the figures for clarity, the simple wiring involved in the present invention is easily understood by one skilled in the art. The PC board 64 controls the electrical components of the toothbrush 10. The motor 14 has terminals 66, 68 that are also wired to the PC board 64. Similarly, the battery 22 has battery terminals 70, 72, 74, 75 that are wired to the PC board 64. Thus, the first switch 12 is actuated by an operator who presses a switch cover 76 that moves a switch button 78 into contact with a component 80 of the PC board 64. Pressing the switch cover 76 toggles the switch 12 between the "off" position and the "automatic" position.

The handle portion 13 also includes a drive shaft seal 82 and a seal support 84. The drive shaft seal 82 helps to ensure that fluid does not reach the electrical components of the toothbrush 10. Because the battery 22 is of the rechargeable type, a light emitting diode (LED) 86, seen in FIG. 3, is provided to indicate to the user when the battery 22 is being charged. The LED 86 is provided with a translucent cover 88 to allow the user to see the LED 86 which would otherwise be covered by the first housing 28. The battery 22 is held in place by a spring assembly 90 and an end cap 92. The end cap 92 is provided with an O-ring seal 94 to further ensure that fluids do not reach the electrical components of the toothbrush 10. Also included in the handle portion 13 is a flat element 96 attached to the first housing 28 to allow the toothbrush 10 to be laid on a flat surface such that the bristle head 18 remains pointing upward. This helps to keep the toothbrush 10 stationary on a surface that is not level, and keeps the bristle head 18 from contacting the surface, which may not be clean. Aesthetic features 98 are added to enhance the visual appeal of the toothbrush 10.

The reciprocating movement of the drive shaft 38 is guided by a bushing 100. The actual movement of the drive shaft 38 resembles a typical slider crank mechanism. The motor 14 has a rotating motor shaft 102 that has a spur gear 104 attached to it. The spur gear 104 intermeshes with and rotates a ring gear 106 that has integrally attached to it a cam 108. The ring gear 106 and the cam 108 are held in a second casing portion 110 with a pin 112. The cam 108 rotates within a cam follower 114 that is attached to the drive shaft 38. Thus, the rotational motion of the motor shaft 102 is translated into reciprocating motion of the drive shaft 38. When the removable head portion 16 is attached to the handle portion 13, the yoke 36 connects to a head 116 on the drive shaft 38 such that the shaft 32 reciprocates along with the drive shaft 38. This in turn moves the pinion 40 along the rack 42 and causes the bristle head 18 to translate and rotate simultaneously.

Figure 7:
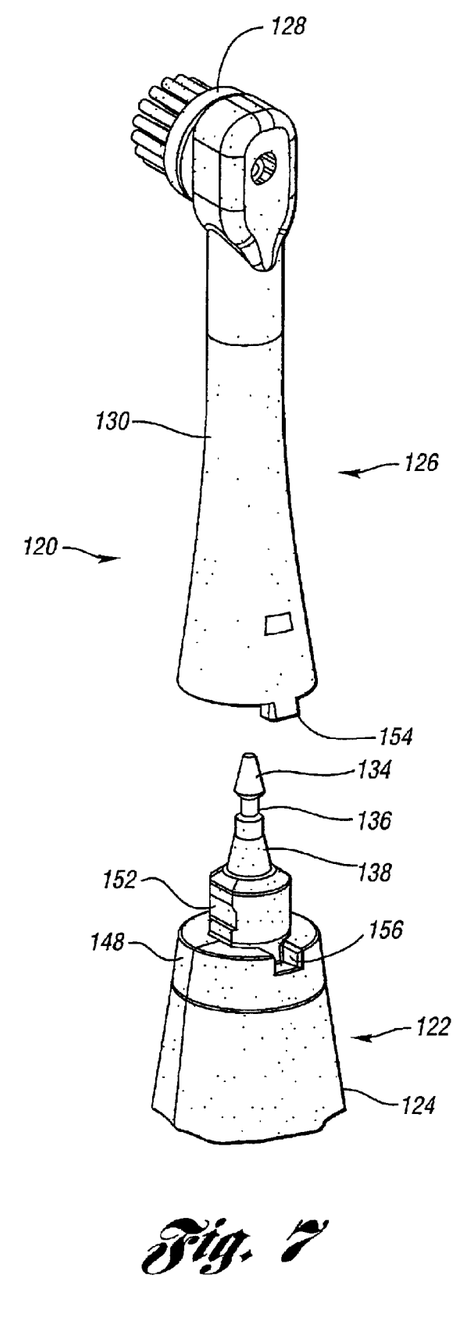
FIG. 7 shows a perspective view of a portion of a toothbrush in accordance with a second embodiment of the invention.
Figure 9:
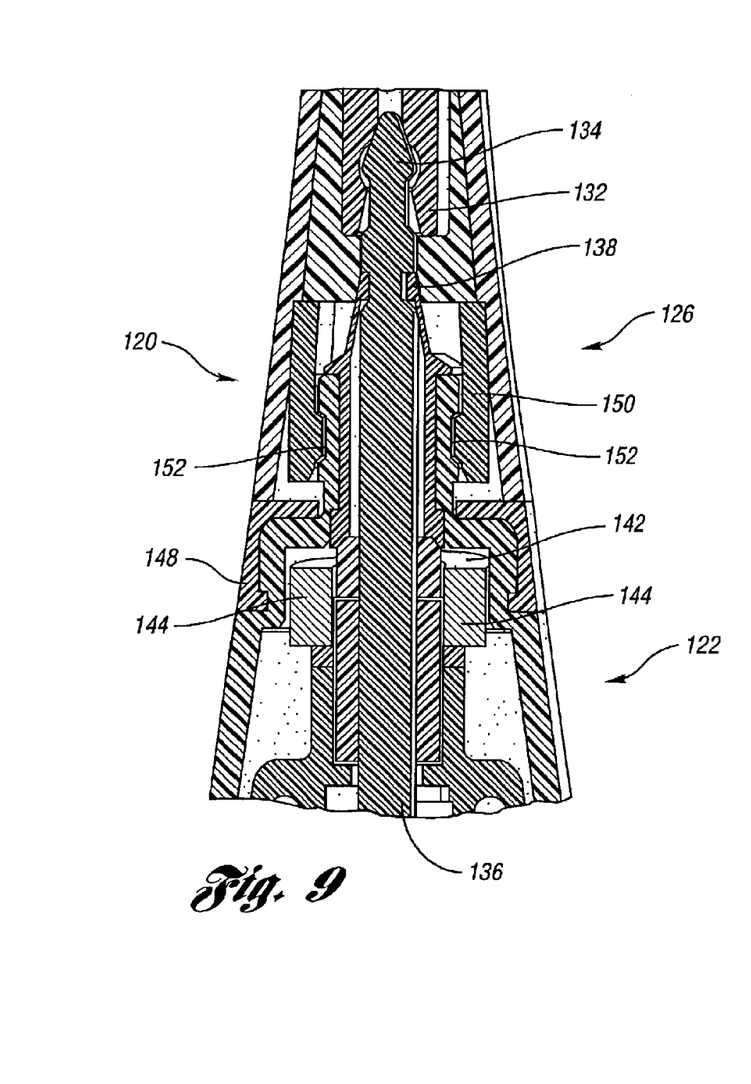
FIG. 9 shows a sectional view of a portion of the toothbrush shown in FIG. 7.
Figure 10:
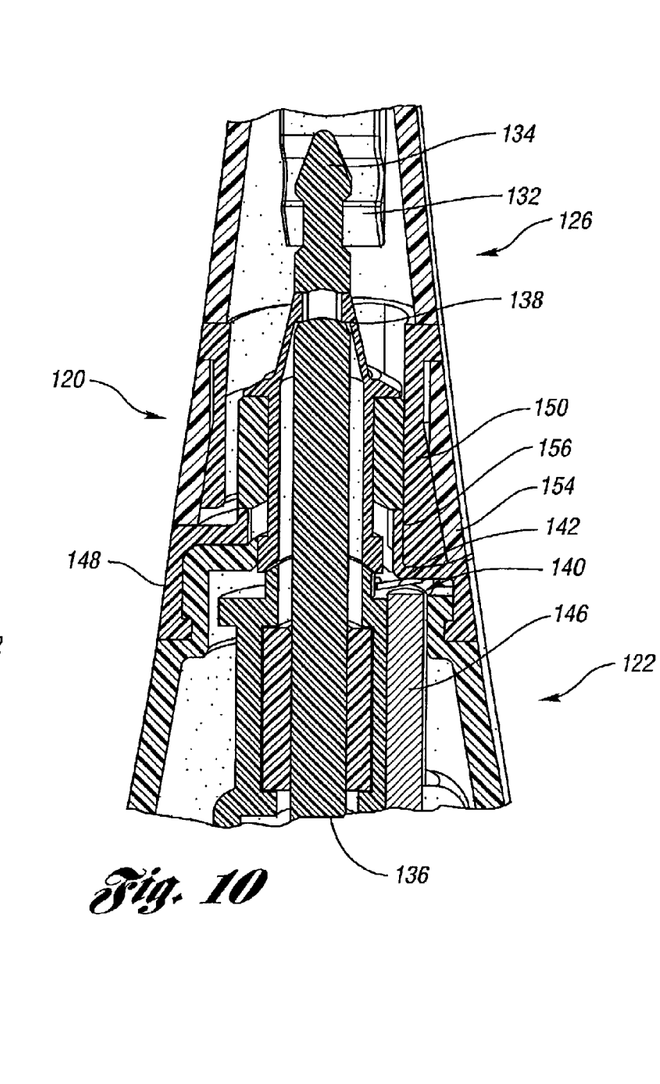
FIG. 10 shows a sectional view of a portion of the toothbrush shown in FIG. 7, rotated approximately 90 degrees from the view shown in FIG. 9.

FIG. 7 shows a portion of a toothbrush 120 in accordance with a second embodiment of the present invention. As in the first embodiment, the toothbrush 120 comprises a handle portion 122 that has a first housing 124 and a removable head portion 126 that has a bristle head 128 and a second housing 130. In this embodiment, the drive mechanism within the replaceable head portion 126 is the same as in the preferred embodiment. This includes a shaft and a pinion which interfaces with a rack to drive the bristle head 128. A yoke 132, seen in FIGS. 9 and 10, connects to a head 134 of a drive shaft 136 which reciprocates when a motor (not shown) is engaged. A seal 138 is disposed around the drive shaft 136 to protect the electrical components of the toothbrush 120 from contamination by fluids.

Figure 8:
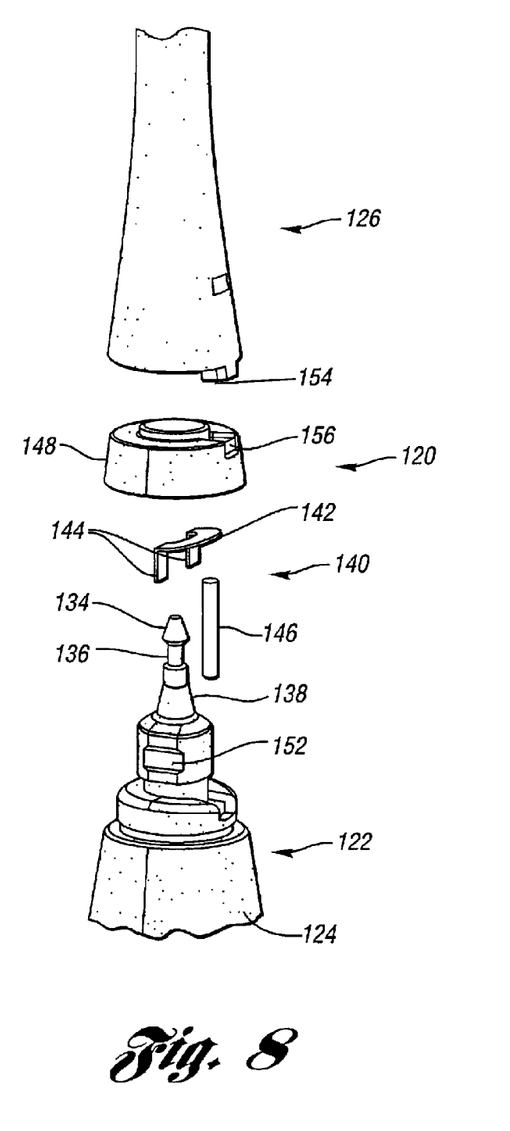
FIG. 8 shows a partially exploded view of a portion of the toothbrush shown in FIG. 7.

The toothbrush 120 includes an automatic mode of operation with a first switch (not shown) that is configured as in the previous embodiment. To facilitate automatic operation, the toothbrush 120 has a second switch 140, seen in FIGS. 8 and 10, that includes a contact plate 142 having legs 144 and a contact rod 146. The contact plate 142 and the contact rod 146 are disposed within the handle portion 122 and covered by a pressure sensitive seal 148. Similar to the contact plates 60, 62 used in the first embodiment, the contact plate 142 and the contact rod 146 are wired to a PC board (not shown).

The method by which the removable head portion 126 attaches to the handle portion 122 is also different from the first embodiment. An adaptor 150, seen in FIGS. 9 and 10, located inside the housing 130 of the removable head portion 126 snaps into recesses 152 in the handle portion 122, see FIG. 9. This attachment allows the removable head portion 126 to be securely attached to the handle portion 122, and at the same time allows for a slight pivotal movement of the removable head portion 126 when the bristle head 128 sufficiently contacts the user's teeth. As consistently used throughout the various embodiments, "sufficiently contacts" merely implies a contact that is sufficient to cause a slight movement of at least a part of the removable head portion 126. As the removable head portion 126 undergoes the slight pivoting motion caused by contact with the user's teeth, a projection 154 pushes into a notch 156 in the pressure sensitive seal 148. As the projection 154 moves into the notch 156, the pressure sensitive seal 148 pushes against the contact plate 142. With the legs 144 held stationary, the contact plate 142 deflects in a spring-like fashion until it contacts the contact rod 146. This actuates the second switch 140 and allows for motorized operation of the toothbrush 120 when it is in the automatic mode. The spring-like deflection of the contact plate 142 also acts to bias it away from the contact rod 146, to disengage the motor when the bristle head is not in contact with the user's teeth.

Figure 11:
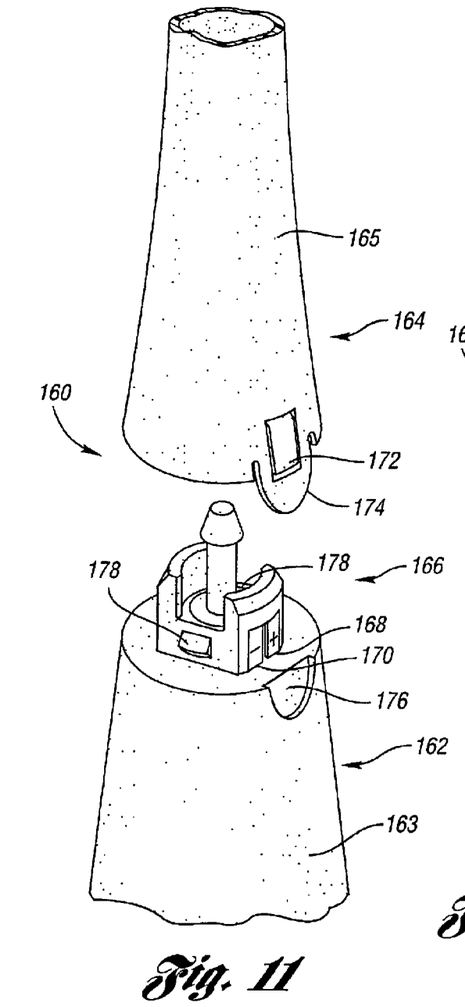
FIG. 11 shows a perspective view of a portion of a toothbrush in accordance with a third embodiment of the invention.
Figure 12:
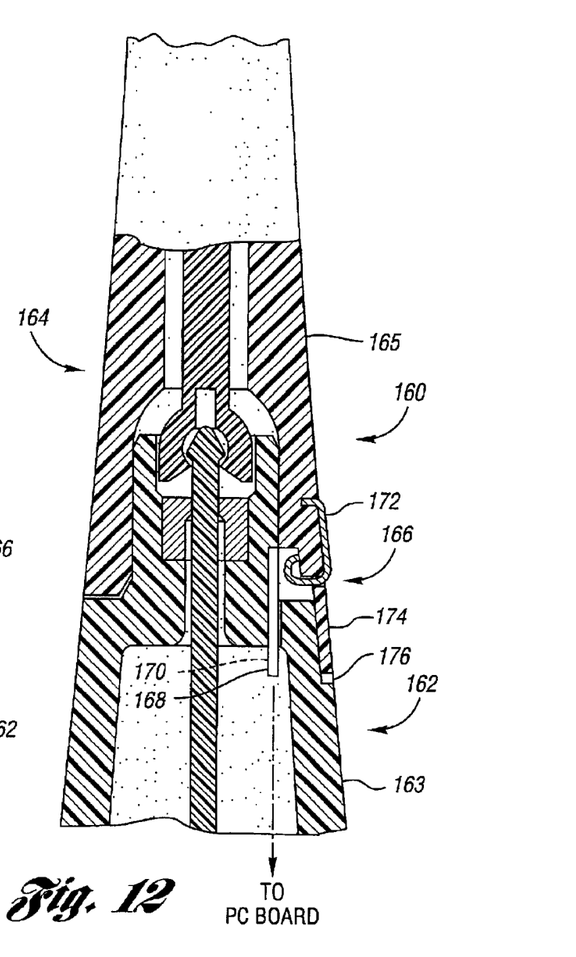
FIG. 12 shows a sectional view of a portion of the toothbrush shown in FIG. 11.

Portions of a third embodiment of the present invention are shown in FIGS. 11 and 12. In this embodiment, a toothbrush 160 includes a handle portion 162 that has a first housing 163 and a removable head portion 164 that has a second housing 165 and a bristle head (not shown). As in the previous embodiments, the toothbrush 160 includes a first switch (not shown) having an "off" position that prevents motorized operation of the toothbrush 160, and an "automatic" position that allows the toothbrush 160 to function in an automatic mode. A second switch 166 comprises two stationary contact plates 168 and 170 and a third contact plate 172. The removable head portion 164 includes a projection 174 that fits into a notch 176 in the first housing 163 of the handle portion 162. The removable head portion 164 attaches to the handle portion 162 at snaps 178. This connection allows the removable head portion 164 be securely attached to the handle portion 162, and at the same time allows for a slight pivotal movement of the removable head portion 164 when a bristle head (not shown) sufficiently contacts the user's teeth. As the removable head portion 164 pivots, the third contact plate 172 contacts, and thereby electrically connects, the stationary contact plates 168, 170. This actuates the second switch 166 and causes motorized operation of the toothbrush 160 when it is in the automatic mode. The projection 174 also acts as a spring as the removable head portion 164 pivots, thereby keeping the third plate 172 biased away from the stationary plates 168, 170 when the bristle head is not in contact with the user's teeth.

Figure 13:
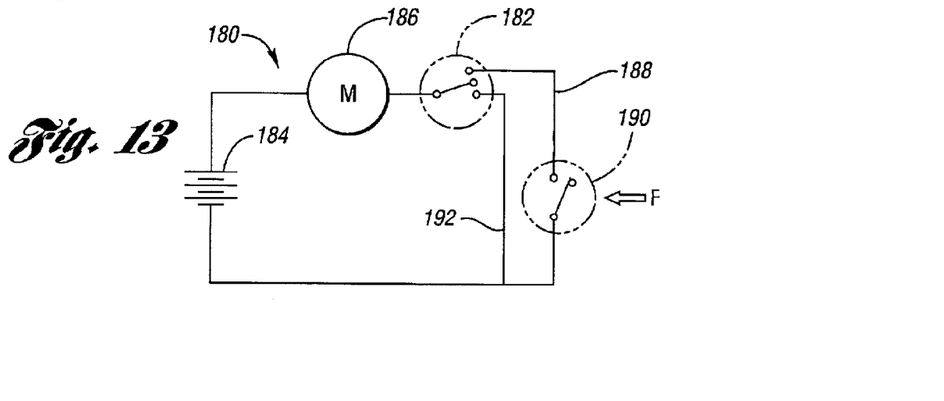
FIG. 13 shows a simple wiring schematic that can be used with any of the various toothbrush embodiments.

FIG. 13 shows a simple wiring schematic 180 of a circuit configuration applicable to any of the embodiments described above. A first switch 182 corresponds to a first switch located within the toothbrush handle. When the first switch 182 is in the first position (open), no current flows from the battery 184 to the motor 186. When the first switch 182 is in the second position, the motor 186 is connected to a circuit 188 so that operation of the motor is dependent on a second switch 190. When a force (F) is applied to actuate (close) the second switch 190, current flows from the battery 184 to the motor 186. This illustrates the automatic mode of operation for the toothbrushes described in detail above. The first switch 182 has a third position however, and in that position the motor 186 is connected to a circuit 192 so that current flow to the motor does not depend on the second switch 190. Rather, when the first switch is in the third position, the motor 186 operates continuously, which is the standard mode of operation for motorized electric toothbrushes.

While these embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A motorized electric toothbrush comprising:
   a handle portion having a first housing;
   a removable head portion having a bristle head and a second housing and selectively attachable to the handle portion; and
   a switch having a first position for preventing motorized operation of the toothbrush and a second position for facilitating motorized operation of the toothbrush, the switch including first and second contact plates disposed to electrically connect, thereby placing the switch in the second position when pressure is exerted on the bristle head, and
   wherein the handle portion includes a pivotable rocker element including an actuator configured to contact one of the contact plates, thereby moving the one contact plate into electrical connection with the other contact plate, when the rocker element pivots in response to a pressure exerted on the bristle head.

2. The electric toothbrush of claim 1, wherein the rocker element further includes an attachment feature configured to facilitate attachment of the removable head portion to the handle portion.

3. The electric toothbrush of claim 1, wherein the actuator includes an actuator arm having a pin thereon for contacting the one contact plate to move it into electrical connection with the other contact plate.

4. A motorized electric toothbrush comprising:
   a handle portion having a first housing;
   a removable head portion having a bristle head and a second housing and selectively attachable to the handle portion;
   a first switch disposed within the handle portion having a first position for preventing motorized operation of the toothbrush and a second position for facilitating automatic operation of the toothbrush; and
   a second switch disposed within one of the housings and including first and second contact plates disposed to electrically connect, thereby actuating the second switch when the toothbrush is used by an operator, thereby causing motorized operation of the toothbrush when the first switch is in the second position, and
   wherein the handle portion includes a pivotable rocker element including an actuator configured to contact one of the contact plates, thereby moving the one contact plate into electrical connection with the other contact plate, when the toothbrush is used by an operator, thereby pivoting the rocker element.

5. The electric toothbrush of claim 4, wherein the rocker element further includes an attachment feature configured to facilitate attachment of the removable head portion to the handle portion.

6. The electric toothbrush of claim 4, wherein the actuator includes an actuator arm having a pin thereon for contacting the one contact plate to move it into electrical connection with the other contact plate.

7. A motorized electric toothbrush comprising:
   a handle portion having a first housing;
   a removable head portion having a bristle head and a second housing and selectively attachable to the handle portion;
   a first switch disposed within the handle portion having a first position for preventing motorized operation of the toothbrush, a second position for facilitating automatic operation of the toothbrush, and a third position for continuous motorized operation of the toothbrush; and
   a second switch disposed within one of the housings and including first and second contact plates disposed to electrically connect, thereby actuating the second switch when the toothbrush is used by an operator, thereby causing motorized operation of the toothbrush when the first switch is in the second position, and
   wherein the handle portion includes a pivotable rocker element including an actuator configured to contact one of the contact plates, thereby moving the one contact plate into electrical connection with the other contact plate, when the toothbrush is used by an operator, thereby pivoting the rocker element.

8. The electric toothbrush of claim 7, wherein the rocker element further includes an attachment feature configured to facilitate attachment of the removable head portion to the handle portion.

9. The electric toothbrush of claim 7, wherein the actuator includes an actuator arm having a pin thereon for contacting the one contact plate to move it into electrical connection with the other contact plate.

* * * * *